United States Patent [19]

Hara et al.

[11] Patent Number: 4,840,966

[45] Date of Patent: Jun. 20, 1989

[54] METHOD OF TREATING HYPERTENSION

[75] Inventors: Yukihiko Hara, Shizuoka; Tateo Suzuki, Sendai, both of Japan

[73] Assignee: Mitsui Norin Co., Ltd., Tokyo, Japan

[21] Appl. No.: 160,026

[22] Filed: Feb. 25, 1988

[30] Foreign Application Priority Data

Mar. 3, 1987 [JP] Japan .................................. 62-48387

[51] Int. Cl.$^4$ ............................................. A61K 31/35
[52] U.S. Cl. ....................................................... 514/456
[58] Field of Search ......................................... 514/456

[56] References Cited

U.S. PATENT DOCUMENTS

| 4,004,038 | 1/1977 | Wickremasinghe | 426/422 |
| 4,105,784 | 8/1978 | Okada | 514/456 |
| 4,613,672 | 9/1986 | Hara | 549/399 |
| 4,673,530 | 6/1987 | Hara | 252/398 |

FOREIGN PATENT DOCUMENTS

| 506600 | 10/1954 | Canada | 549/399 |
| 0015417 | 2/1978 | Japan . | |
| 60-156614 | 8/1985 | Japan | 514/456 |
| 61-130285 | 6/1986 | Japan | 514/456 |

OTHER PUBLICATIONS

Chem. Abstracts 80:119307x, (1974).
Chem. Abstracts 76:70341(e), (1972).
Chem. Abstracts 96:6481M, (1982).
Chem. Abstracts 77:58728Z, (1975).
Chem. Abstracts 69:77066h, (1968).
Sanderson, The Chemistry of Tea and Tea Manufacturing, Recent Advances in Phytochemistry No. 5, pp. 247-255, (1972).
Hudson, Naturally-Occurring Antioxidants in Leaf Lipids, J. Sci. Food Agric., 1980, 31, 646-650.
The Merck Index-"Tenth Edition", p. 8932, (1983).
Haslem, Vegetable, Tannings, Recent Advances in Phytochemistry, vol. 12, Biochemistry of Plant Phenolics, pp. 475-499.
Tanizawa et al., Natural Antioxidants I. Antioxidative Components of Tea Leaf (Thea sinensis L.), Chem. Pharm. Bull. 32(5)2011-2014, (1984).
Matsuzaki et al., Antioxidative Activity of Tea Leaf Catechins, Nippon Nogeikugaku Kaishi, vol. 59, No. 2, pp. 129-134, 1985.
Chipaut et al., Antoxidants for Use in Foods, In: Lundberg, W. D., Autoxidation and Antioxidants, vol. II, (New York, J. Wiley and Sons, 1962), pp. 511-512.
Harborne et al., The Flavonoids, Academic Press, (1975), pp. 550-553.
Chipault et al., the Antioxidant Properties of Natural Spices, Food Research, vol. 17, (1952), pp. 46-55.
OMORI et al., "Effect of Anaerobically Treated Tea (Gabaron Tea) on Blood Pressure of Spontaneously Hypertensive Rats", Nippon Nogeikaguku Kaisha 11/87, 61(11), pp. 1449-1450.
Chemical Abstracts 108:74006b, (1987).
Chemical Abstracts 108:7388w, (1987).
Tsushida et al., "Production of a New Type Tea Containing a High Level of $\gamma$-Aminobutyric Acid", Nippon and Nogeikagaku Kaishi, 7/1987, 61(7), p. 871-22.
Chemical Abstracts 107:153147f, (1987).

*Primary Examiner*—Allen J. Robinson
*Attorney, Agent, or Firm*—Frishauf, Holtz, Goodman & Woodward

[57] ABSTRACT

A method of treating hypertension to reduce blood pressure or to maintain blood pressure at a desired level comprising administering to the patient an effective amount to maintain or lower blood pressure of tea polyphenols. The tea polyphenols include (−)-epigallocatechin gallate, free theaflavin, theaflavin monogallate A, theaflavin monogallate B and theaflavin digallate.

10 Claims, 4 Drawing Sheets

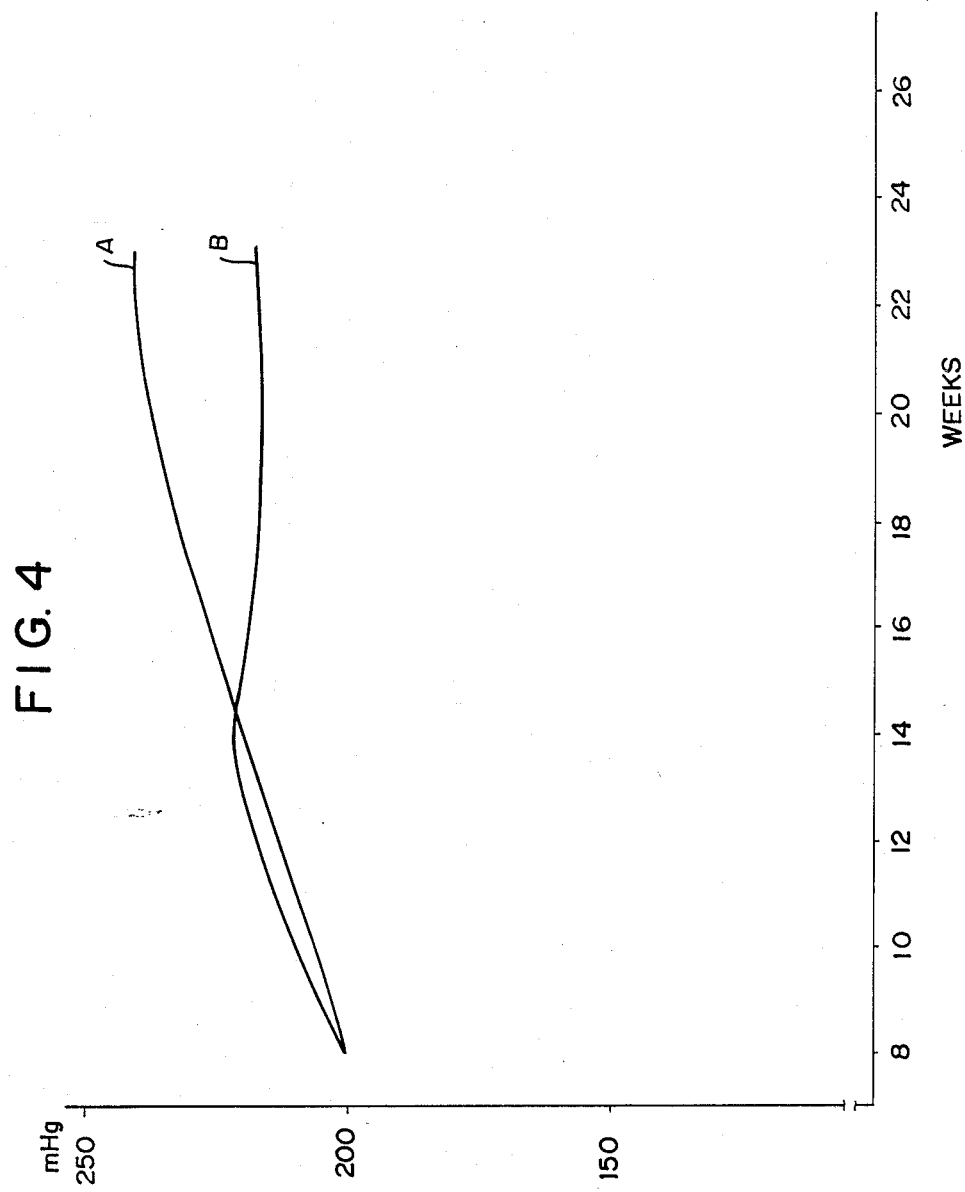

METHOD OF TREATING HYPERTENSION

BACKGROUND OF THE INVENTION

Angiotensin I converting enzyme (ACE) is an exopeptidase related to the blood pressure control system known as reninangiotensin system. This enzyme converts inactive decapeptide angiotensin I by cleaving carboxylic terminal dipeptide to give active octapeptide angiotensin II, the most potent naturally occurring pressor substance known. The enzyme also inactivates the potent vassodepressor peptide bradikinin. Therefore ACE plays physiologically very important roles in maintenance of the blood pressure system from the elevating side. Much work has been done to find out effective ACE inhibitors in the hope to reduce the blood pressure of essential hypertensive patients of reninangiotensin dependent types. The most effective inhibitor ever developed is SQ 14,225, an artificially synthesized dipeptide known as Captopril. Today Captopril is effectively dosed orally in common clinical therapy for various kinds of essential hypertensions. Yet this compound has only about 10 years history and some side effects are quoted in some cases. Therefore good hypotensive method with mild but sure effect which could be used lifelong without any fear of side effects are wanted.

SUMMARY OF THE INVENTION

With an object to discover a novel therapeutic method for hypertension as mentioned above, the inventors have continued extensive investigations of natural products to discover a substance capable of exhibiting the desired effect without the problems usually ensue in chemically synthesized compounds. As a result, the inventors have arrived at a discovery that by the use of specific tea polyphenols, i.e. (−)-epigallocatechin gallate and/or theaflavins, with specified treating method, the blood pressure of essential hypertensive patients could be reduced. Thus the subject of the present invention is the method of treating the hypertension comprising administering to the patients an effective amount to maintain or lower blood pressure of tea polyphenols in a pharmaceutically acceptable carrier.

BRIEF DESCRIPTION OF THE DRAWING

FIG. 4 is a graph showing the hypotensive effect of epigallocatechin gallate mixed in the diet and fed to Spontaneously Hypertensive Rats.

DETAILED DESCRIPTION OF THE PREFERRED EMBODIMENTS

The tea polyphenols as the principal of ACE inhibitor include (−)-epigallocatechin gallate expressed by the structural formula (I)

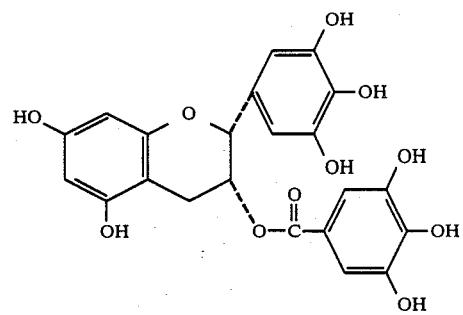

free theaflavin expressed by the structural formula (II)

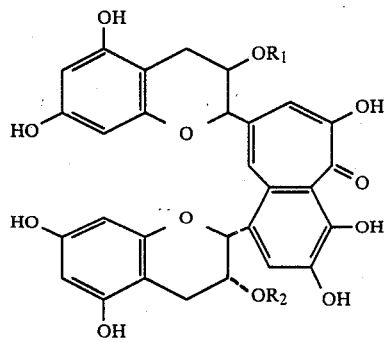

where $R_1$ and $R_2$ are each a hydrogen atom, theaflavin monogallate A expressed by the structural formula (II) where $R_1$ is a group X and $R_2$ is a hydrogen atom, theaflavin monogallate B expressed by the structural formula (II) where $R_1$ is a hydrogen atom and $R_2$ is a group X and theaflavin digallate expressed by the structural formula (II) where $R_1$ and $R_2$ are each a group X. Where X being a 3,4,5-trihydroxy benzoyl group of the formula

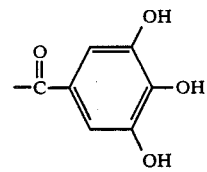

As is apparent from the structural formula, theaflavins are the dimerric compounds of catechins that are synthesized oxidatively in the black tea manufacturing process.

The tea polyphenols as the principal ingredients of the ACE inhibitor of the invention can be prepared from tea leaves in a following procedure.

The tea raw material for the tea polyphenols are not particularly limited to a specific type of tea, usually tea leaves, for example fresh tea leaves, unfermented tea leaves, semi-fermented tea leaves, green teas of medium grade, instant green teas and the like. The tea leaves are first washed with a mixture of a hydrophobic and a hydrophilic organic solvent to remove caffeine and pigments. The tea leaves, after drying by evaporating the solvents, are then moistened by adding a small amount of water and brought into contact with an organic solvent so that the ingredients including the catechin compounds are transferred into the organic solvent. The thus obtained organic solution is concentrated by evaporating the organic solvent and the concentrated solution is subjected to the high-performance liquid chromatography on a reversed-phase partition column using a 0-25:0-35:65-85 by volume mixture of acetone, tetrahydrofuran and water as eluant to effect isolation of epigallocatechin gallate. Details of this procedure are described in Japanese Patent Kokai Nos. 60-13780 (U.S. Pat. No. 4,613,672) and 61-130285.

Figure 1:
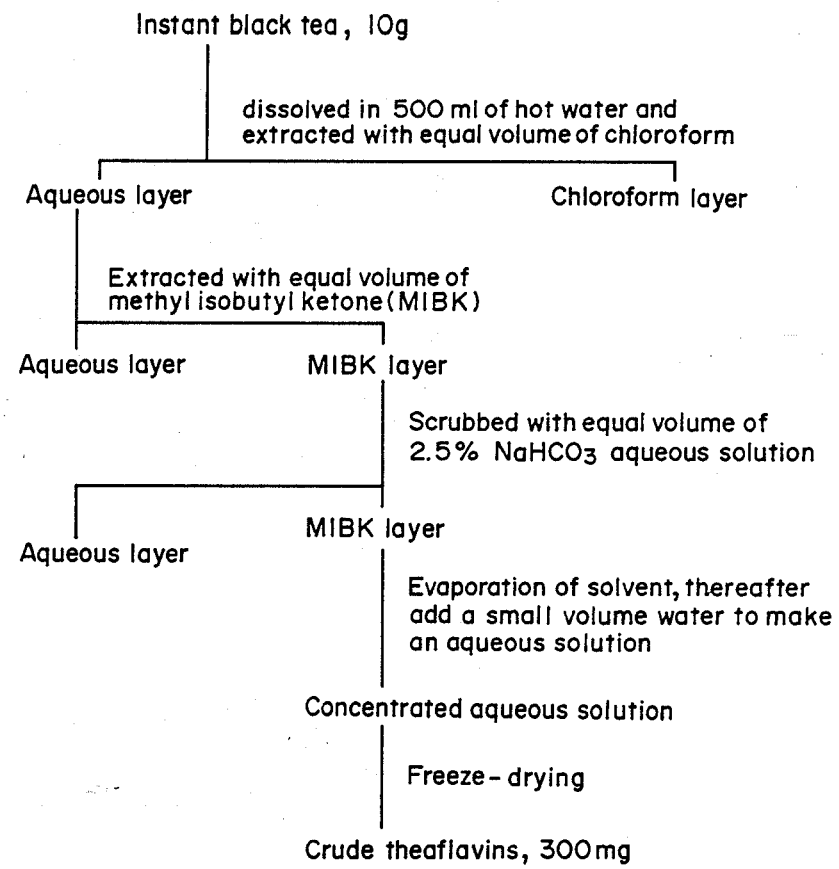
FIG. 1 is a flow chart illustrating the process for the isolation of the theaflavins from tea.
Figure 2:
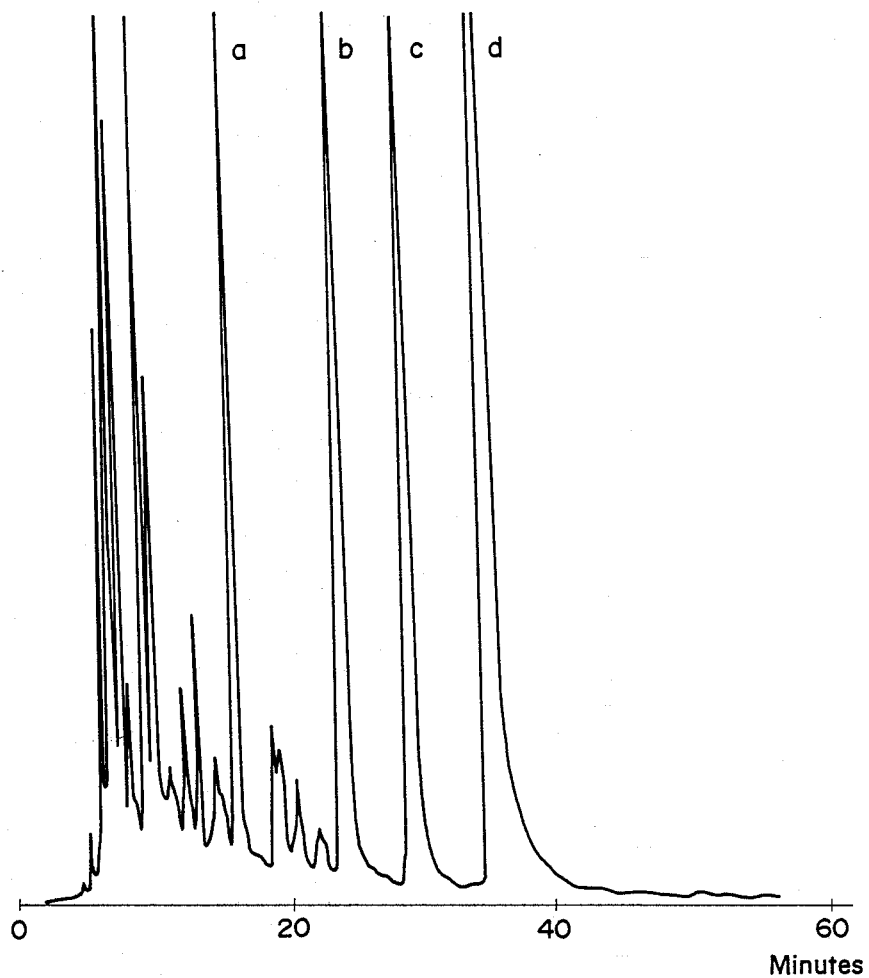
FIG. 2 is a chromatogram of the theaflavins obtained by the high-performance liquid chromatography.

The theaflavin derivatives expressed by the above given structural formula (II) can be prepared from semi-fermented teas, fermented teas or instant black teas, for example, in a procedure illustrated by the flow chart in FIG. 1 to give a crude theaflavin mixture followed by the high-performance liquid chromatography to isolate the respective theaflavin derivatives including the free theaflavin, theaflavin monogallate A, theaflavin monogallate B and theaflavin digallate. FIG. 2 illustrates a high-performance liquid chromatogram of the crude theaflavin mixture in which the peaks indicated by the symbols a, b, c and d correspond to the fractions of the free theaflavin, theaflavin monogallate A, theaflavin monogallate B and theaflavin digallate, respectively. Following are the conditions for fractionation of these ingredients by the high-performance liquid chromatography.

Instrument: Model LC4A manufactured by Shimadzu Seisakusho
Chromatographic column: YMC A-312 ODS, 6 mm × 15 mm
Mobile phase: 21:3:76 by volume mixture of acetonitrile, ethyl acetate and 0.05% aqueous solution of phosphoric acid
Flow rate: 1 ml/minute These theaflavin derivatives are colored in orange and their ultraviolet absorption spectra have the absorption maxima at wavelengths of 380 and 460 nm.

EXAMPLE 1

The activity of the tea polyphenols for the inhibition of ACE was examined using Hip-His-Leu as the substrate on behalf of Angiotensin I. Thus, the substrate was admixed with the sample solution and the ACE obtained from renal cortex of pig and shaken at 37° C. so as to produce dipeptide which was made fluorescent by the addition of O-phthal aldehyde and its intensity was measured. To describe more particularly, 240 μl of the substrate solution (46.6 mg/19.2 ml buffer solution) were admixed with 20 μl of ACE (106 mU/5 ng) and 50 μl of the sample solution to effect the reaction in a conventional manner. The activity of ACE inhibition was expressed by the equation $$(S-B)/A \times 100 \, (\%),$$

in which S was the intensity of the fluorescence in the above described procedure with the sample solution, A was the value of the blank test by replacing the sample solution with the same volume of water and B was the value obtained by replacing the enzyme solution with the same volume of pure water. Namely, the value of this equation is equal to 100% when no ACE inhibitor is added and equal to 0% when inhibition of the activity of ACE is complete. Table 1 below summarizes the concentrations in μM of several inhibitor compounds required for 50% inhibition of ACE and carboxypeptidase A which is an enzyme exhibiting enzymatic activities similar to ACE.

TABLE 1

| Inhibitor | Concentration for 50% inhibition of ACE activity, μM | Concentration for 50% inhibition of carboxypeptidase A activity, μM |
|---|---|---|
| Captopril | 0.078 | — |
| (—)-Epigallocatechin gallate | 90 | 3000 |
| Free theaflavin | 400 | >5000 |
| Theaflavin monogallate A | 115 | >5000 |
| Theaflavin monogallate B | 110 | >5000 |
| Theaflavin digallate | 35 | 5000 |

As is clear from Table 1, the tea polyphenols as the principal ingredients of the inventive ACE inhibitor exhibit strong inhibiting power of the ACE while they have very low inhibiting power against carboxypeptidase A indicating that their inhibiting power is specific against ACE. The strongest ACE inhibitor among the above named tea polyphenols is theaflavin digallate and, though not comparable with captopril, the concentration thereof required for 50% inhibition of the ACE activity are sufficiently low so that these inhibitors, which are natural products with long history of daily consumption, could be used without particular care to side effects.

Figure 3:
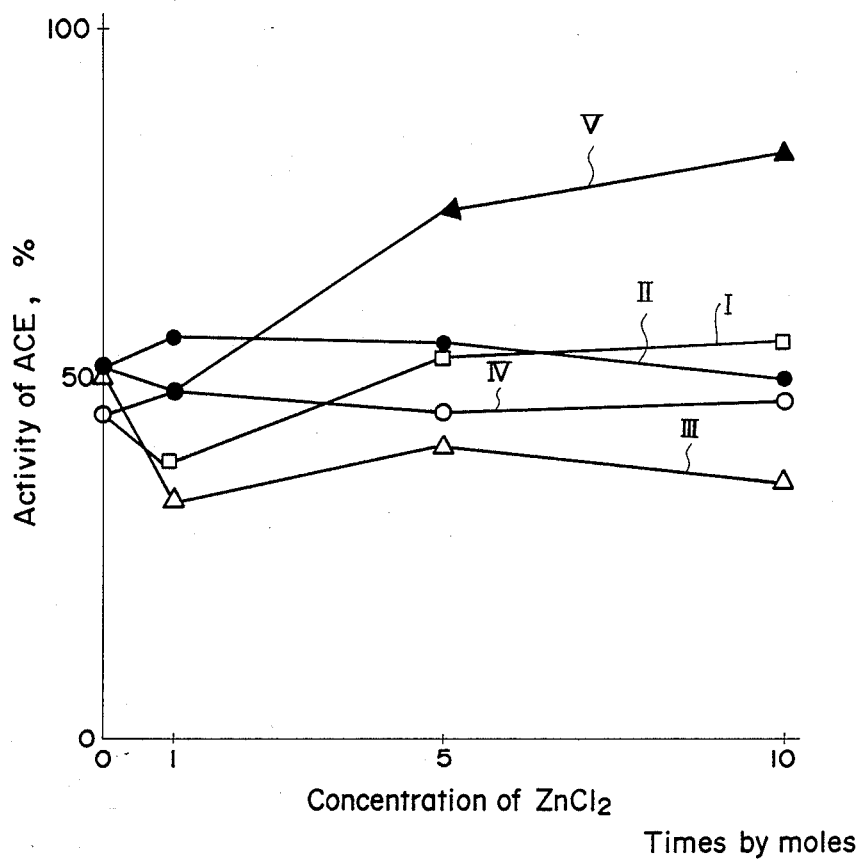
FIG. 3 is a graph showing independence of tea polyphenols from chelation with free zinc ions on the ACE inhibiting activity.

Since ACE is a zinc containing enzyme and tea polyphenols are most likely to chelate with zinc ions, the possibility that ACE will be inhibited by catechins or theaflavins by means of simple chelation was considered. In order to investigate the foregoing possibility, an overdose of zinc chloride was added to the tea polyphenolic samples before they were mixed with ACE. In the test each sample contained the tea polyphenol at the 50% inhibition dose level. Zinc chloride was added to samples in an amount (i) equal to, (ii) 5 times and (iii) 10 times (in moles) of the polyphenolic concentration. ACE activity was measured in the same manner as described before. FIG. 3 shows the results taking the activity of ACE as the ordinate to see the function of zinc chloride. The curves I, II, III, IV and V show the results for epigallocatechin gallate, free theaflavin, theaflavin monogallate A, theaflavin monogallate B and theaflavin digallate, respectively.

These figures indicate that free zinc ions have little to do with ACE inhibiting activity of tea polyphenols. It could be concluded that the ACE inhibiting activity of these polyphenols are likely not due to the chelation of these compounds to the zinc contained in ACE.

As it is understood from the above description, the ACE inhibiting effect of certain tea polyphenols is specific to ACE and therefor therapeutic utilization of these compounds seems very promising for the treatment of hypertensive patients since they could be used without fear of any side effects as a natural product.

EXAMPLE 2

Three SHR (Spontaneously Hypertensive Rats) of 8 weeks old were fed on the diet which consisted of 99.5% of normal diet and 0.5% of epigallocatechin gallate mixed together. As a control two SHR of the same stock were fed on a 100% normal diet. After seven weeks feeding the blood pressure of tea polyphenol fed group levelled off while the blood pressure of the control group continued to rise. In FIG. 4, the curve A denotes the systolic blood pressure of control group while B denotes the systolic blood pressure of test group.

EXAMPLE 3

By administering various does of epigallocatechin gallate orally to the mice of male ICR strain of 8 weeks old, it was found that the $LD_{50}$ of one week was 2,314 mg/kg.

In order to provide the tea polyphenols to hypertensive adult patients, it is preferable to administer about 2 to about 5 grams of the tea polyphenols orally per day. This may be administered in one dose or in a series of doses. It is understood that somewhat larger or lower amounts of the tea polyphenols, for example about 0.5 to about 10 grams per day could be used in the treatment and/or maintenance of hypertensive patients depending upon the patient size and individual conditions which includes the patient's ability to effectively utilize the tea polyphenols. The tea polyphenols may be administered by a tablet or capsule or in the form of a solid. To get this amount of the tea polyphenols by tea-drinking is impossible since only 7 grams of epigallocatechin gallate is contained in 100 grams of green tea and 1 gram of theaflavins is extractable from 100 grams of black tea. Caffeine consist of 3% of made tea and it is far easier to be extracted than polyphenols by hot water. Therefore adverse effect of caffeine is apparent by drinking so much of tea.

The tea polypehnols would be provided in the form of pharmaceutical compositions which also contain at least one pharmaceutical carrier and/or adjuvant including fillers such as lactose, and glucose; binders such as liquid starch, liquid CMC; disintegrator such as starch, crystal cellulose; and smoothing agents such as magnesium or talc, etc. The composition may be formed into tablets or capsules which may be covered with a layer of sugar if desired.

EXAMPLE 4

An example of a tablet preparation of a pharmaceutical composition follows:
  epigallocatechin gallate: 500 mg
  anhydrous silica: 80 mg
  crystal cellulose: 140 mg
  lactose: 200 mg
  magnesium stearate: 2 mg These are made into one tablet according to the known practice.

What is claimed is:

1. A method of treating hypertension to reduce blood pressure or to maintain blood pressure at a desired level comprising administering to a patient in need thereof, an effective amount of at least one tea polyphenol selected from the group consisting of (−)-epigallocatechin gallate, free theaflavin, theaflavin monogallate A, theaflavin monogallate B and theaflavin digallate to maintain or lower blood pressure.

2. The method of treating hypertension as claimed in claim 1 wherein the tea polyphenols are used together with at least one pharmaceutically acceptable carrier.

3. The method of treating hypertension as claimed in claim 1 wherein said tea polyphenol is (−)-epigallocatechin gallate.

4. The method of treating hypertension as claimed in claim 1 wherein said tea polyphenol is free theaflavin.

5. The method of treating hypertension as claimed in claim 1 wherein said tea polyphenol is theaflavin monogallate A.

6. The method of treating hypertension as claimed in claim 1 wherein said tea polyphenol is theaflavin monogallate B.

7. The method of treating hypertension as claimed in claim 1 wherein said tea polyphenol is theaflavin digallate.

8. The method of treating hypertension as claimed in claim 1 wherein 0.5 to about 10 grams of tea polyphenols are administered per day.

9. The method of treating hypertension as claimed in claim 1 wherein 2 to 5 grams of tea polyphenols are administered per day.

10. The method of claim 3 wherein said pharmaceutically acceptable carrier is lactose, glucose, liquid starch or crystal cellulose.

* * * * *

UNITED STATES PATENT AND TRADEMARK OFFICE
CERTIFICATE OF CORRECTION

PATENT NO. : 4,840,966

DATED : June 20, 1989

INVENTOR(S) : HARA et al

It is certified that error appears in the above-identified patent and that said Letters Patent is hereby corrected as shown below:

Column 6, line 38 (claim 10):

Change "of claim 3" to read --of claim 2--.

Signed and Sealed this

Nineteenth Day of May, 1992

Attest:

DOUGLAS B. COMER

*Attesting Officer*   *Acting Commissioner of Patents and Trademarks*